(12) United States Patent
Yakopson

(10) Patent No.: US 6,725,691 B2
(45) Date of Patent: Apr. 27, 2004

(54) THERAPEUTIC STOCKINGS

(75) Inventor: Simon Myron Yakopson, Hickory, NC (US)

(73) Assignee: BSN-Jobst, Charlotte, NC (US)

( * ) Notice: Subject to any disclaimer, the term of this patent is extended or adjusted under 35 U.S.C. 154(b) by 107 days.

(21) Appl. No.: 09/739,943

(22) Filed: Dec. 18, 2000

(65) Prior Publication Data

US 2002/0108405 A1 Aug. 15, 2002

(51) Int. Cl.$^7$ ................................. A41B 11/00
(52) U.S. Cl. ................ 66/178 A; 66/178 R; 2/240
(58) Field of Search ................ 66/182, 185, 187, 66/178 A, 178 R; 2/239, 240, 241

(56) References Cited

U.S. PATENT DOCUMENTS

| | | |
|---|---|---|
| 3,975,929 A | 8/1976 | Fregeolle |
| 4,015,448 A | 4/1977 | Knohl |
| 4,021,860 A | 5/1977 | Swallow et al. |
| 4,027,667 A | 6/1977 | Swallow et al. |
| 4,048,818 A | 9/1977 | Cueman |
| 4,057,880 A | 11/1977 | Matthews et al. |
| 4,069,515 A | 1/1978 | Swallow et al. |
| 4,086,790 A | 5/1978 | Hanrahan, Jr. et al. |
| 4,106,313 A | 8/1978 | Boe |
| 4,180,065 A | 12/1979 | Bowen |
| 4,180,869 A | 1/1980 | Pedergrass et al. |
| 4,521,484 A | 6/1985 | Li |
| 4,561,267 A | 12/1985 | Wilkinson et al. |
| 5,164,262 A | 11/1992 | Kobayashi et al. |
| 5,335,517 A | 8/1994 | Throneburg et al. |
| 5,352,518 A | 10/1994 | Muramoto et al. |
| 5,412,957 A | 5/1995 | Bradberry et al. |
| 5,509,282 A | 4/1996 | Ferrell, Jr. |
| 5,643,660 A | 7/1997 | Price et al. |
| 5,737,943 A | 4/1998 | Bernhardt |
| 5,823,014 A | 10/1998 | Kobayashi et al. |
| 5,823,195 A | 10/1998 | Shook et al. |
| 5,972,502 A | 10/1999 | Jessee et al. |

FOREIGN PATENT DOCUMENTS

| | | |
|---|---|---|
| EP | 1 039 001 A | 9/2000 |
| FR | 2 588 890 A | 4/1987 |
| FR | 2 805 459 A | 8/2001 |

*Primary Examiner*—Danny Worrell
(74) *Attorney, Agent, or Firm*—Alston & Bird LLP

(57) ABSTRACT

A knitted therapeutic medical compression stocking made from courses of bi-component fibers inlaid courses of spandex yarn. The use of bi-component yarns, in particular, crimped yarns having an elastomeric core preferably of a polyurethane and a thermoplastic sheath preferably of a polyamide when knit with inlaid courses of bare spandex, covered spandex, or spandex covered with a bi-component yarn forms therapeutic medical stockings that provide excellent compression control. In addition, these therapeutic stockings are more transparent than conventional therapeutic stockings. The therapeutic stockings of the present invention may be knit on a conventional circular hosiery knitting machine.

12 Claims, 5 Drawing Sheets

THERAPEUTIC STOCKINGS

FIELD OF THE INVENTION

Background of the Invention

The present invention relates to knitted therapeutic medical compression garments. More particularly, the present invention relates to knit therapeutic graduated compression stockings having courses of crimped bi-component yarns having an elastomeric core with a thermoplastic sheath and inlay courses containing spandex yarn.

Therapeutic medical compression stockings have been used on a relatively wide scale to assist in the prevention of venous diseases and/or embolism in a patient. The purpose of such stockings is to overcome the elevated internal pressures within a human extremity caused by gravity or disease processes.

The pressure gradient stocking and its use are well documented in the literature. The custom pressure gradient stocking was developed by Conrad Jobst a sufferer of venous disease. Mr. Jobst found relief from his problem while standing in a swimming pool. Mr. Jobst reasoned that the water pressure in the pool, which increases with depth, cancelled out the internal pressure in the veins of his leg. Jobst and others have identified a need to apply a relatively large compressive force in proximity to the ankle. See, page 535 of the article entitled "Conrad Jobst and the Development of Pressure Gradient Therapy for Venous Disease." Also see, the article entitled "Treatment of venous disease— The innovators" at page 681 thereof quoting from an article by J. Horner, et al. entitled "Value of graduated compression stockings in deep venous insufficiency," Br Med J. 1980; zz: 820–1 wherein it is stated "the greater the compression gradient between the ankle and calf produced by the stocking, the lower the ambulatory pressures." Cited in U.S. Pat. No. 5,823,195.

Therapeutic medical graduated compression stockings are designed to provide sufficient external circumferential counter pressure to maintain the normal venous and lymphatic pressures at a given level in the extremity, thus assisting the movement of venous blood and lymph from the extremity. Another important effect of compression is the reduction of the venous volume. Reduction of venous volume leads to an increase of the venous flow velocity. Gerwen H J L van. *Pressure gradient tolerance in compression hosiery.* Katholike Universiteit Nijmegen. 1994, pp. 103–105.

Furthermore, while the exact mechanism(s) of action of gradient compression therapy remain unknown improvements in skin and subcutaneous tissue microcirculatory hemodynamics may contribute to the benefits of compression therapy. The direct effect of compression on subcutaneous pressure is a plausible mechanism. Edema reduction and edema prevention is the goal in patients with chronic venous insufficiency, lymphedema, and other edema causing conditions. Subcutaneous pressures increase with elastic compression. Nehler M R, Moneta G L, Woodard D M, et al. Perimalleolar subcutaneous pressure effects of elastic compression stockings. *J Vasc Surg* 1993;18(5):783–88. This rise in subcutaneous tissue pressure should act to counter transcapillary Starling forces, which favor leakage of fluid out of the capillary.

For instance, gradient compression stockings 20 mmHg and above have demonstrated the following effects in persons with venous insufficiency:

Improved venous hemodynamics

Prolonged (more normalized) venous refill time (VRT). Samson R H, Scher L A, Veith F J, et al. Compression stocking therapy for patients with chronic venous insufficiency. *J Cardiovasc Surg* 1985;26:10.

Reduced venous volume and increased venous flow velocity Reduction and control of edema. Dale W A. The Swollen Limb in *Current Problems In Surgery*, edited by Mark M Ravitch, et al. 1973 Year Book Medical Pub, Chicago. p. 29–31.

Most of the patients suffering from minor to moderate varicosities, moderate edema, superficial thronbophlebitis, and post sclerotherapy need to use stockings with the compression at ankle in the range from 15–20 to 20–30 mm Hg. More complicated and severe cases require pressure of 40 mm Hg and higher.

A variety of therapeutic medical graduated compression stockings are on the market today. The stockings of various descriptions have been proposed. Unfortunately, therapeutic stockings, in order to provide the necessary compression, are often thick and rather unsightly or have other drawbacks. An example of a therapeutic stocking is described in U.S. Pat. No. 3,975,929 which describes a thigh length anti-embolism stocking made with alternating courses of covered spandex yarn on a circular hosiery knitting machine. Another example of a therapeutic stocking is described in U.S. Pat. No. 4,069,515 to Swallow, et al., which discloses a non-slip therapeutic stocking having a covered elastomeric yarn (spandex core-nylon covering) inlaid into every other course of the jersey knit stitches made of stretch nylon. In particular, the Swallow patent describes the foot portion as having alternating courses of jersey knit stitches of non-elastomeric yarn. One of these yarns is a Z-twist stretch nylon and the other is an S-twist nylon. A covered elastomeric yarn such as a single covered elastomeric yarn having a 280 denier spandex core and covered with nylon 6 yarn is preferably inlaid into every other course of the jersey stitches.

The use of bi-component crimped yarns is known in the manufacture of pantyhose. Such garment construction is described in U.S. Pat. No. 5,352,518 to Muramoto, et al., who teach a stocking having a bi-component core and sheath type yarn wherein the sheath is composed of a fiber forming a thermoplastic polymer and the core is composed of a fiber forming elastomer. It is stated that the filament has excellent elastic properties, a small surface friction coefficient and a matting effect due to diffusion reflection of light caused by rough surfaces, and is agreeable when worn in the form of a knitted textile structure, particularly as a lady's stocking.

SUMMARY OF THE INVENTION

A principle feature of the present invention is the provision of a therapeutic medical compression stocking made with bi-component fibers. It has been found that the use of bi-component yarns, in particular, those crimped yarns having an elastomeric core and a thermoplastic sheath when knit with inlaid courses of spandex or spandex covered with a bi-component yarn form therapeutic stockings that provide excellent compression control. In addition, these therapeutic stockings are more transparent than conventional therapeutic stockings. The therapeutic stockings of the present invention may be knit on a conventional circular knitting machine.

In a first preferred embodiment every course of the therapeutic stocking is knit with a crimped bi-component yarn having an elastomeric core and a thermoplastic sheath. Courses of an inlay yarn of spandex are provided at least every third course. In a second embodiment, the therapeutic stocking is knit with every other course being the crimped bi-component yarn and the inlay yarn is spandex present in every course. The alternate courses are covered spandex yarn. It was found that the use of spandex yarns in combination with the bi-component yarn enables the reduction in size of the spandex used in the inlay courses and maintains the desired compression.

In yet another embodiment of the present invention, there is provided a knitted therapeutic stocking comprising a crimped bi-component yarn in every course and an inlay yarn of spandex covered with a bi-component yarn. In a fourth embodiment there is provided a knitted therapeutic stocking comprising a crimped bi-component yarn in every other course and inlay course of spandex covered with a bi-component yarn.

It has been found that the therapeutic medical compression stockings of this invention provide a smooth, silky, cool and supple hand of fabric; easier donning, lighter weight, good durability and very good compliance with patient needs.

It is an object of the present invention to provide a therapeutic stocking having excellent compression by using an improved bi-component crimped yarn of the present invention.

Another object of the present invention is to provide an improved air-permeable therapeutic stocking because the spandex inlay yarns do not need to be covered.

Yet another object of the present invention is to provide a therapeutic stocking having improved transparency.

Other features and advantages of the present invention will become apparent in the following detailed description of the embodiments of the invention when taken in conjunction with the accompanying drawings.

BRIEF DESCRIPTION OF THE DRAWINGS

Figures 1, 2, 3:
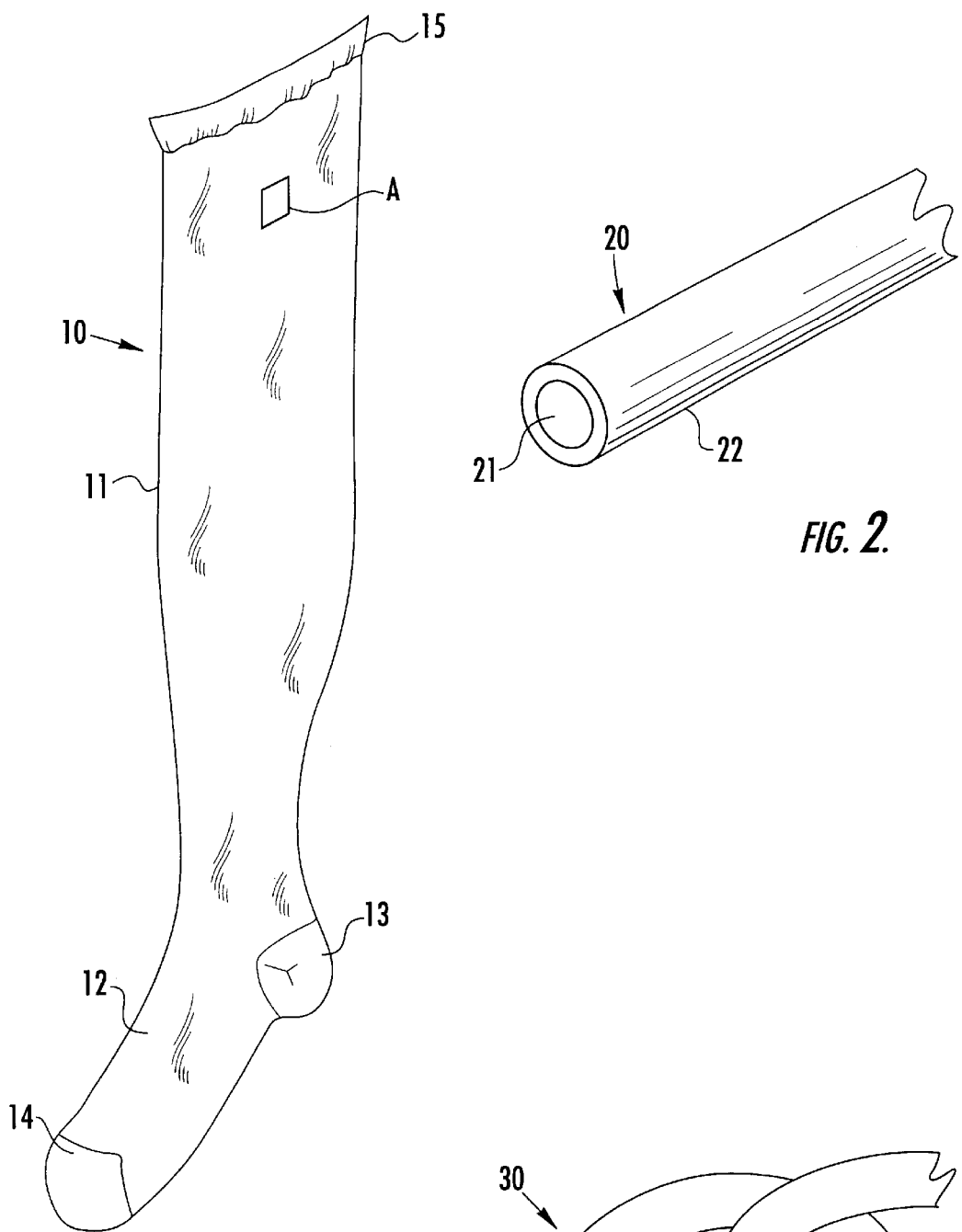
Figure 4:
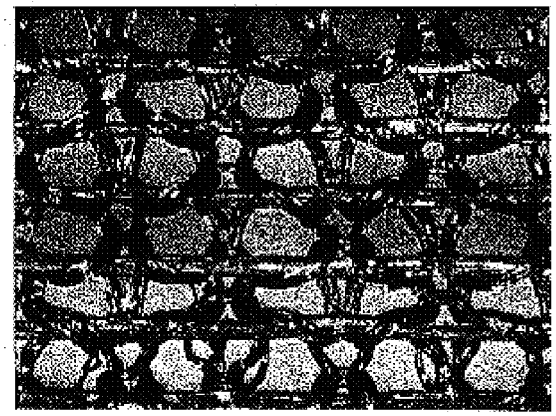
Figure 5:
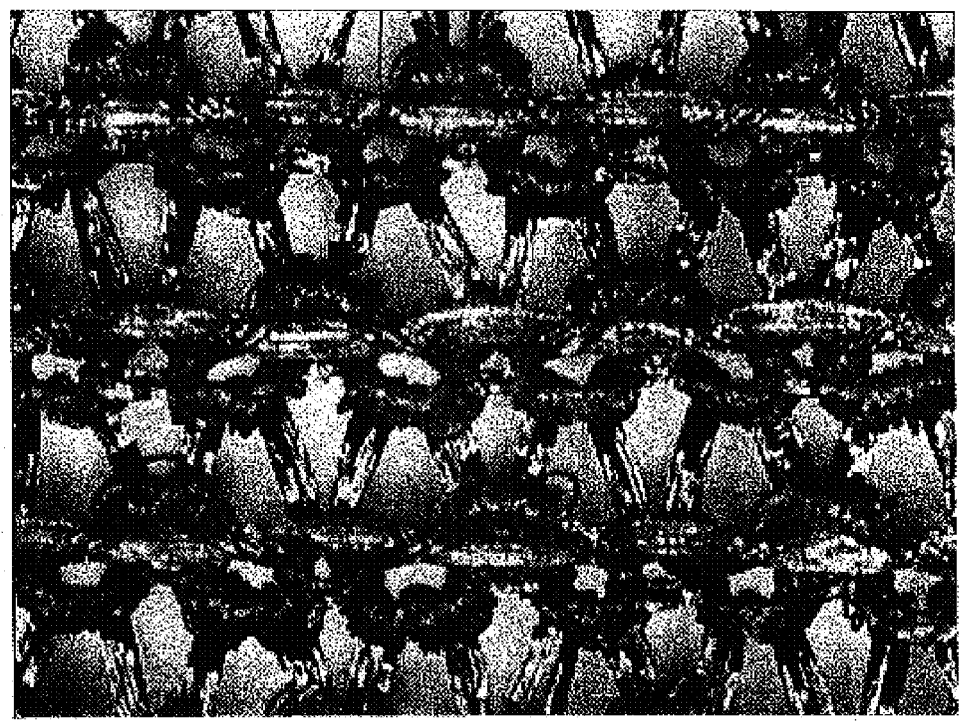
Figure 6:
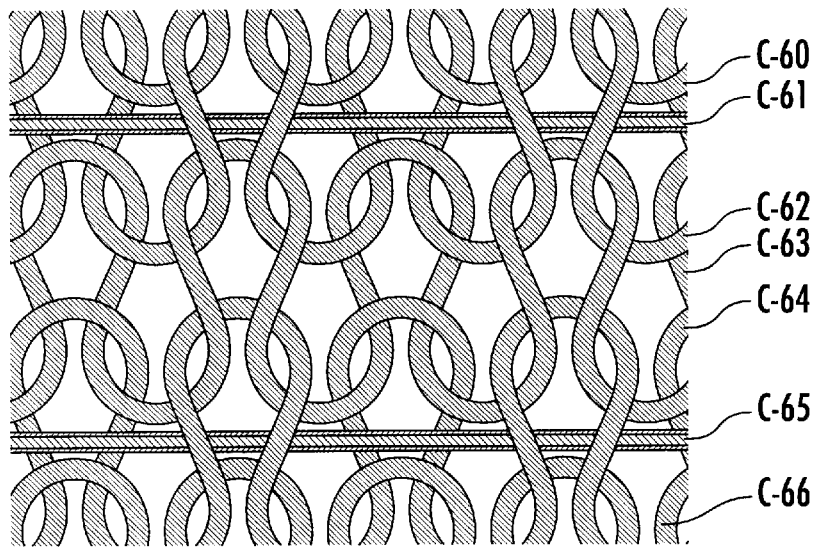
Figure 7:
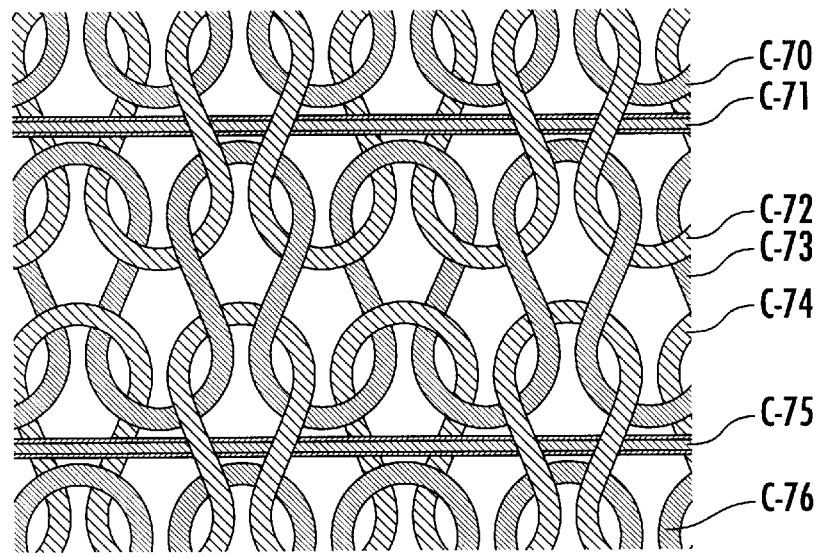
Figure 8A:
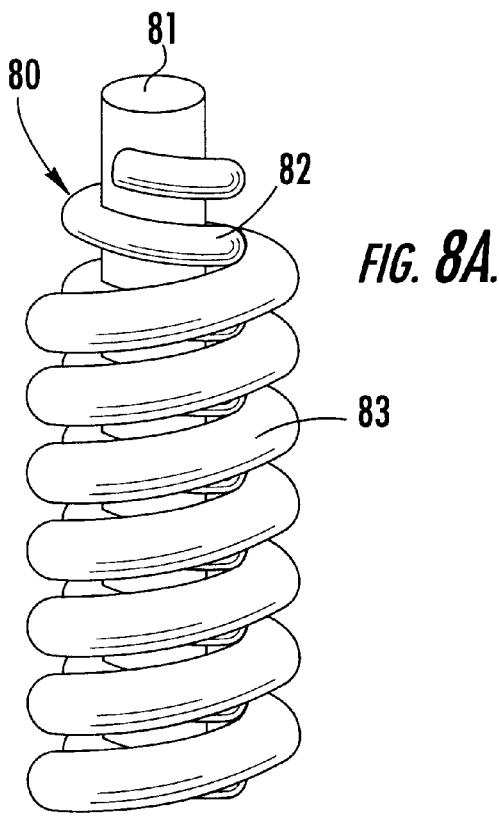
Figure 8B:
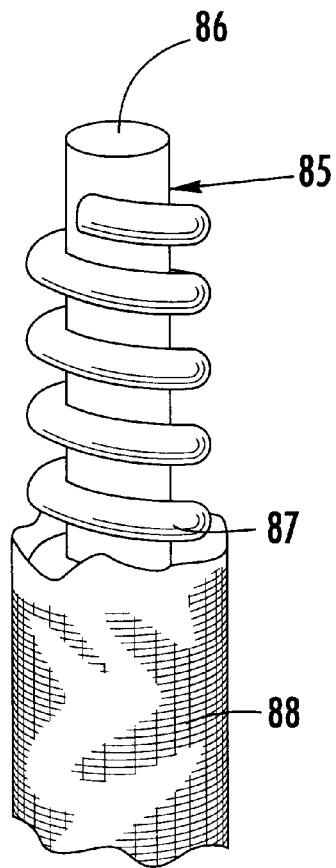

Having thus described the invention in general terms, reference will now be made to the accompanying drawings, which are not necessarily drawn to scale, and wherein:

FIG. 1 is an isometric view of a therapeutic stocking of the present invention;

FIG. 2 shows a bi-component, uncrimped yarn used to knit the therapeutic stockings of the present invention illustrating;

FIG. 3 shows the bi-component yarn of FIG. 2 used to make the therapeutic stockings of this invention in its crimped condition;

FIG. 4 is a photomicrograph of a fragmentary portion of a fabric made of bi-component yarns showing a first embodiment of a knit fabric used to make the therapeutic stocking of the present invention taken in the area of rectangle A in FIG. 1;

FIG. 5 is a photomicrograph of a fragmentary portion of a fabric made of bi-component yarns showing a second embodiment of a knit fabric used to make the therapeutic stocking of the present invention taken in the area of rectangle A in FIG. 1;

FIG. 6 is an enlarged view of a fragmentary portion of a fabric made of bi-component yarns showing a third embodiment of a knit fabric used to make the therapeutic stocking of the present invention taken in the area of rectangle A in FIG. 1;

FIG. 7 is an enlarged view of a fragmentary portion of a knit fabric made of bi-component yarns showing a fourth embodiment of the fabric used to make the therapeutic stocking of the present invention taken in the area of rectangle A in FIG. 1;

FIG. 8A shows a spandex yarn covered with a double bi-component yarn used in the inlay courses of the therapeutic stockings of the fourth embodiment of the present invention; and FIG. 8B shows a spandex yarn covered with a single covering of bi-component yarn used in the inlay courses of the therapeutic stockings of the fourth embodiment of the present invention.

Figure 9A:
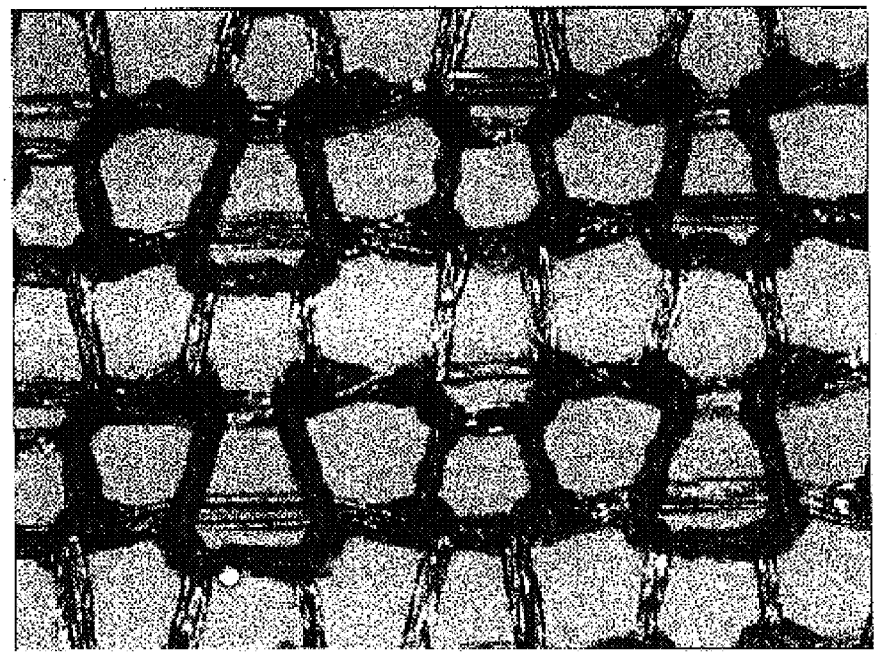

FIG. 9A shows a spandex yarn core covered with two bi-component yarns used in the inlay courses of the therapeutic stockings of an embodiment of the present invention.

Figure 9B:

FIG. 9B, shows an embodiment of the inlay yarn having a spandex core covered with a single layer of bi-component yarn used in the inlay courses of the therapeutic stockings of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

There is shown in FIG. 1 the therapeutic medical compression stocking 10 of the present invention. The stocking 10 includes a leg portion having an enlarged upper section 11 and a foot portion 12. The foot portion 12 including a heel pocket 13 and a toe pocket 14. The upper section 11 of the medical stocking can be provided with an upstanding and integrally knit band 15 for knee length or thigh length stockings, or a sewn in anti-slip band. Alternatively, the stockings can be an integral part of a panty hose garment.

An example of a bi-component yarn used to make the therapeutic medical compression stockings is shown in FIG. 2. The yarn 20 is composed of an elastomeric core 21, that is preferably a polyurethane, more preferably a cross-linked polyurethane. Any such known polyurethane as polycarbonate-urethanes, polyactone-urethanes and polyether-urethanes may be used as the polymer that forms the polyurethane core in the form of a homopolymer or copolymer of polyurethane or a mixture thereof. As a yarn forming thermoplastic polymer forming the sheath 22 of the yarn a polyamide such as nylon 6, nylon 66, or nylon 12 is preferred. Additionally, polyolefins also can be suitably employed. The core/sheath bi-component weight ratio is in the range between 20:80 and 80:20, with 50:50 by weight especially preferred. The core/sheath bi-component ratio is preferably within the range between 5/1 and 90/1, more preferably between 10/1 and 50/1, by cross-sectional area. Especially preferred are those polyurethane yarns disclosed in U.S. Pat. No. 5,164,262, incorporated herein by reference.

Additionally, the bi-component yarn may have an eccentric configuration such as those yarns disclosed in U.S. Pat. No. 5,352,518. The use of eccentric yarns allows the attainment of latent crimping properties that allow coil-like crimps to be produced by the crimp development treatment. An illustration of a bi-component yarn in crimped configuration is shown in FIG. 3 wherein the crimped yarn 30 has an elastomeric core 31 and a polyamide sheath 32. The bi-component yarns used to make the therapeutic stocking of this invention may be self-crimping yarns that form crimps, including helical coil-like crimps spontaneously. The yarns may also be externally treated such as by using an elevated temperature, or a swelling agent. Such bi-component yarns are commercially available under the name Sideria® available from Kanebo of Japan.

The elastomeric yarn used in the alternating or inlay courses is preferably spandex, such as Globe's Clearspan® manufactured by Globe Manufacturing Inc., Fall River, Mass. Other spandex yarns that may be used includes Lycra® spandex manufactured by DuPont, or Dorlastan® spandex manufactured by Bayer, or any other applicable spandex yarn. In some embodiments of the invention the spandex yarn is covered with a bi-component yarn such as described above or with nylon yarns as shown in FIG. 8A and FIG. 8B. In some embodiments of the invention the spandex yarn can be covered with one (so-called single covered as shown in FIG. 8A) or two layers (double covered as shown in FIG. 8B) of nylon or bi-component yarn.

The fragmentary view A of a portion of fabric structure in the leg section 11 of the stocking (FIG. 4) is illustrates a first preferred embodiment of the therapeutic stocking of this invention as if the fabric were stretched in both coursewise and walewise directions. As shown in FIG. 4, each course (C-40, C-42, C-44, C-46 and C-48) of the therapeutic stocking is knit with a crimped bi-component yarn. Courses (C-41, C-43, C-45, C-47 and C-49) of inlay yarn are spandex. Courses of inlay yarn are laid in at least every three courses. It should be understood, however, that if more compression is needed the inlay courses may be used more frequently as shown by inlay yarns in every course in FIG. 4. It was found that the combination of bi-component yarns and spandex enabled the reduction in size of the spandex core used in the inlay courses and maintain the desired compression.

As shown in the second embodiment, that of FIG. 5 illustrating a fragmentary view A if a portion of fabric structure in the leg section 11 of the stocking, the therapeutic stocking is knit with alternating rows of jersey knit stitches of crimped bi-component polyurethane yarn. The intervening rows are courses of covered elastic yarn. A covered elastic yarn is a single covered elastic yarn, such as spandex with a covering yarn singly or double wound around the elastic yarn. Any polyamides such as nylon 6 and nylon 66, which are used for common polyamide fibers, can be used as the material of the polyamide filaments constituting the covering yarn. As shown in FIG. 5, every other course (C-50, C-53, and C-56) of the therapeutic stocking is knit with a crimped bi-component yarn. The intervening courses (C-52, C-55 and C-58) are of covered elastic yarn. Courses (C-51, C-54 and C-57) of inlay yarn are spandex.

In FIG. 6 there is shown a third embodiment of the fabric structure A in the leg section 11 of FIG. 1 used to knit the therapeutic stockings of the present invention. In this embodiment every course (C-60, C-61, C-63, C-64 and C-66) of the knit stocking is a bi-component yarn. Each course of inlay yarn (C-61 and C-65) is comprised of spandex covered with a bi-component yarn. Such construction enables the reduction in the size of spandex in each course.

There is shown in FIG. 7 a fourth embodiment of the fabric structure A used to knit the therapeutic stockings of the present invention. As shown in FIG. 7, every other course (C-70, C-73 and C-76) of the therapeutic stocking is knit with a crimped bi-component yarn. The intervening course (C-72 and C-74) are of covered elastic yarn. Courses (C-71 and C-75) of inlay yarn are spandex covered with a bi-component yarn. Preferred yarns are shown in FIG. 8A and FIB. 8B.

In FIG. 9A there is shown a spandex yarn core covered with two bi-component yarns used in the inlay courses of the therapeutic stockings of the fourth embodiment of the present invention. As shown in FIG. 9A, the yarn 80 has a spandex yarn component 81. The spandex yarn is covered with one layer of bi-component yarn 82 wound in one direction and then a second bi-component yarn 83 wound in the other direction. In FIG. 9B, there is also shown another embodiment of the inlay yarn 85 having a spandex core 86 covered with a single layer of bi-component yarn used in the inlay courses of the therapeutic stockings of the fourth embodiment of the present invention.

EXAMPLE 1

A therapeutic stocking was knit with a jersey knit structure on a conventional circular knit hosiery machine. The leg yarn was a crimped bi-component yarn having a polyurethane core with a polyamide sheath in each course as shown by the fabric structure of FIG. 4. The inlay yarn was bare spandex. This stocking was then compared to the stocking presently on the market. The result is shown in Table 1.

TABLE 1

| Property | Prior Art[1] | Invention |
| --- | --- | --- |
| Knit structure | Jersey with bare spandex inlay | Jersey with bare spandex inlay |
| Leg yarn | Covered, polyurethane core and polyamide over wrap | Bi-component, polyurethane core with polyamide sheath[2] |
| Total (Sum) linear density of leg yarn | 50 | 50 |
| Denier (Linear Density) Weight of polyurethanecore part (yarn) | 20 | 25 |
| Denier (Linear Density) of cover part (yarn) | 30 (double covering with 15 den nylon) | 25 (sheath) |
| Linear density of inlay yarn | 105 den polyurethane yarn[4] | 70 den polyurethane yarn[3] |
| Total linear density of polyurethane yarns | 125 | 95 |
| Pressure at ankle | 18.5 | 21.6 |

TABLE 1-continued

| Property | Prior Art[1] | Invention |
|---|---|---|
| Donning force at ankle, kg[5] | 3.3 | 2.5 |
| Weight, g, one leg size medium | 26 | 17.8 |
| Suppleness/stiffness - expert evaluation | Less supple | Very supple. Not stiff. Thin |
| Hand | Not silky, feels harsher than prototype, slightly rubbery especially inside a stocking | Smooth, silky, cool, not rubbery |
| Air permeability, ASTM-737 cm$^3$/s/cm$^2$ | 730 | 876 |

[1]Jobst UltraSheer 15–20 medical hosiery.
[2]Sideria yarn from Kanebo.
[3]162C Lycra from DuPont.
[4]S85 Glospan from Globe Manufacturing Co.
[5]These measurements were taken according to the test set forth in PCT/U.S.99/21676 filed September 17, 1999.

EXAMPLE 2

To further demonstrate advantages in donning, and fabric's air-permeability and suppleness the stockings were knitted from bi-component and conventionally covered yarns. Yarns of similar deniers were used and conditions of knitting were adjusted to produce stockings with similar pressure values.

TABLE 2

| Property | Prior Art[1] | Invention |
|---|---|---|
| Knit structure | Jersey with bare spandex inlay | Jersey with bare spandex inlay |
| Leg Yarn | 20 den Lycra double covered with 20 den nylon | Bi-component |
| Total leg yarn denier | 60 | 50 |
| Denier of inlay yarn | 140 | 140 |
| Total linear density of polyurethane yarns | 160 | 165 |
| Pressure at ankle | 25.1 | 23.9 |
| Donning force at ankle, kg | 3.7 | 2.3 |
| Air-permeability | 598 | 746 |
| Stiffness, g, ASTM | 18.5 | 9.2 |

[1]Jobst UltraSheer 20–30 medical hosiery.

Again it can be easily seen that use of bi-component yarn results in significant improvements in stocking's donning, and fabric's air-permeability and suppleness.

As can be seen from the results obtained, the first embodiment provides a therapeutic stocking that has superior properties, which is very supple and has a smooth silky cool hand.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A knitted therapeutic medical compression stocking comprising courses of a crimped bi-component yarn having an elastomeric core and a thermoplastic sheath wherein the core/sheath bi-component ratio is within the range between 20:80 and 80:20 by weight, and inlaid courses of an elastomeric yarn.

2. The knit therapeutic stocking according to claim 1 wherein said core of said bi-component yarn is a polyurethane and said sheath portion is a polyamide.

3. The knit therapeutic stocking according to claim 1 wherein the core/sheath bi-component ratio is about 50:50 by weight.

4. The knit therapeutic stocking according to claim 1 wherein said elastomeric yarn inlay courses are spandex.

5. The knit therapeutic stocking according to claim 1 wherein said elastomeric inlay courses are bare spandex or spandex covered with yarn other than an elastomeric yarn.

6. A knitted therapeutic medical compression stocking comprising courses of a crimped bi-component yarn having an elastomeric core and a thermoplastic sheath and inlaid courses of an elastomeric yarn wherein said elastomeric inlay courses are spandex covered with a bi-component yarn having a polyurethane core and a polyamide sheath.

7. The knit stocking of claim 1 wherein said bi-component yarn is present in every course.

8. The knit stocking of claim 1 wherein said bi-component yarn is present in every other course.

9. The knit stocking of claim 2 wherein said bi-component yarn is present in every course and said inlay courses are spandex.

10. The knit stocking of claim 2 wherein said bi-component yarn is present in every other course and said inlay courses are spandex.

11. A knitted therapeutic medical compression stocking comprising at least every course being a crimped bi-component yarn having an elastomeric core and a thermoplastic sheath and inlay courses of spandex covered with a bi-component yarn having a polyurethane core and a polyamide sheath.

12. A knitted therapeutic medical compression stocking comprising at least every other course being a crimped bi-component yarn having an elastomeric core and a thermoplastic sheath and inlaid course of an elastomeric yarn.

* * * * *